United States Patent
van der Schoot

[11] Patent Number: 5,646,722
[45] Date of Patent: Jul. 8, 1997

[54] APPARATUS FOR CANDLING EGGS FOR THE PRESENCE OF BLOOD

[75] Inventor: Jelle van der Schoot, Aalten, Netherlands

[73] Assignee: FPS Food Processing Systems B.V., Netherlands

[21] Appl. No.: 556,543

[22] Filed: Nov. 28, 1995

[30] Foreign Application Priority Data

Nov. 29, 1994 [NL] Netherlands .................. 9402001

[51] Int. Cl.$^6$ .................................................. G01N 33/08
[52] U.S. Cl. ............................. 356/53; 356/58; 356/66
[58] Field of Search ............................. 356/53, 62, 64, 356/66, 67, 58; 209/510, 511, 522, 523; 198/370.12, 438, 471.1, 803.5

[56] References Cited

U.S. PATENT DOCUMENTS

| | | | |
|---|---|---|---|
| 2,536,057 | 1/1951 | Hodson et al. | 198/803.5 |
| 2,843,264 | 7/1958 | Pfister | 198/803.5 |
| 3,434,594 | 3/1969 | Husome | 198/370.12 |
| 5,017,003 | 5/1991 | Keromnes et al. | 356/53 |

FOREIGN PATENT DOCUMENTS

| | | |
|---|---|---|
| 2455282 | 11/1980 | France . |
| 603097 | 9/1934 | Germany . |
| 89/06797 | 7/1989 | WIPO . |

*Primary Examiner*—Richard A. Rosenberger
*Attorney, Agent, or Firm*—Larson and Taylor

[57] ABSTRACT

An apparatus for candling eggs travelling along a path for the presence of blood, comprising a lightproof drum which is drivable for rotation around a fixed shaft and wherein detection means are accommodated, the drum having a number of light transmission openings which each have a bellows, the drum in operation having a rotational speed so that the ends of the bellows remote from the drum have a speed corresponding to the speed of travel of the eggs, the drum with the bellows being positioned relative to the path of travel so that in operation, each time during a part of the path of travel of the eggs, the bellows connect to an egg to be inspected, while the detection means are positioned in the drum so that they only receive light that falls into the drum via the egg which is to be inspected and to which the bellows connects, and via the light transmission opening associated with that bellows.

8 Claims, 2 Drawing Sheets

APPARATUS FOR CANDLING EGGS FOR THE PRESENCE OF BLOOD

FIELD OF THE INVENTION

Such an apparatus is for instance described in U.S. Pat. No. 4,063,822.

The invention relates to an apparatus for candling eggs travelling along a path for the presence of blood, comprising at least one light source for shining on the egg to be inspected and detecting means for determining the amount of light falling through the egg.

BACKGROUND OF THE INVENTION

A problem of the known apparatus is formed by the screening of the detection means against scattered light, i.e. light which is not transmitted via the egg but which falls on the detection means directly or via reflection surfaces. For a proper operation of the candling apparatus it is important that the amount of scattered light falling on the detection means is minimized. For this purpose, in U.S. Pat. No. 2,987,182 the path along which the eggs are moved is at least partly screened by a lightproof tunnel, with a light source disposed on one side of the path and detection means disposed on the other side. Because of the presence of the tunnel, the detection means will receive only little scattered light. Nevertheless, the detection means continue to receive a particular amount of scattered light, so that this solution is not yet entirely satisfactory. Moreover, the solution is only practicable in a suitable manner if only one path of travel is present. When several parallel paths of travel are present, the space that will be occupied by the light source and the detection means will lead to a large distance in between the paths or to a great length of the path along which detection means are disposed.

SUMMARY OF THE INVENTION

The object of the invention is to provide an apparatus without the above-described drawbacks. Hence, an apparatus with which eggs can automatically be candled, with no or hardly any scattered light falling on the detection means, and which can moreover be of a very compact design both in the case of a single path of travel and in the case of a number of parallel paths of travel.

To this end, the invention provides an apparatus for candling eggs travelling along a path for the presence of blood. The apparatus includes at least one light source for shining on the egg to be inspected and detection means for determining the amount of light falling through the egg. The detection means are housed in a lightproof drum which is drivable for rotation around a fixed shaft. The drum's surface is provided with a number of light transmission openings, each having a bellows manufactured from lightproof material. In operation, the drum has a rotational speed so that the ends of the bellows remote from the drum have a speed corresponding to the speed of travel of the eggs to be inspected. The bellows are positioned relative to the path along which the eggs travel so that in operation, the bellows connect in a lightproof manner to each egg being inspected, while the detection means are positioned in the drum so that they only receive light that falls into the drum via the egg which is to be inspected and to which the bellows connects, and via the light transmission opening associated with the bellows.

An apparatus having these features can be of a very compact design and offers the advantage that by means of this apparatus candling measurements can be carried out very quickly without scattered light disturbing the measurement. Owing to the presence of the drum, wherein the detection means are accommodated, a number of measurements can simultaneously be carried out on eggs travelling in parallel paths. Because the bellows are for some time connected in a lightproof manner to an egg to be inspected, the measurement can very well be carried out on continuously moving eggs. However, it is obviously also possible to carry out measurements on discontinuously moving eggs.

BRIEF DESCRIPTION OF THE DRAWINGS

Further elaborations of the invention are set forth in the subclaims and will be further explained on the basis of an exemplary embodiment of the apparatus with reference to the accompanying drawings, wherein:

DETAILED DESCRIPTION OF THE PREFERRED EMBODIMENTS

Figure 1:
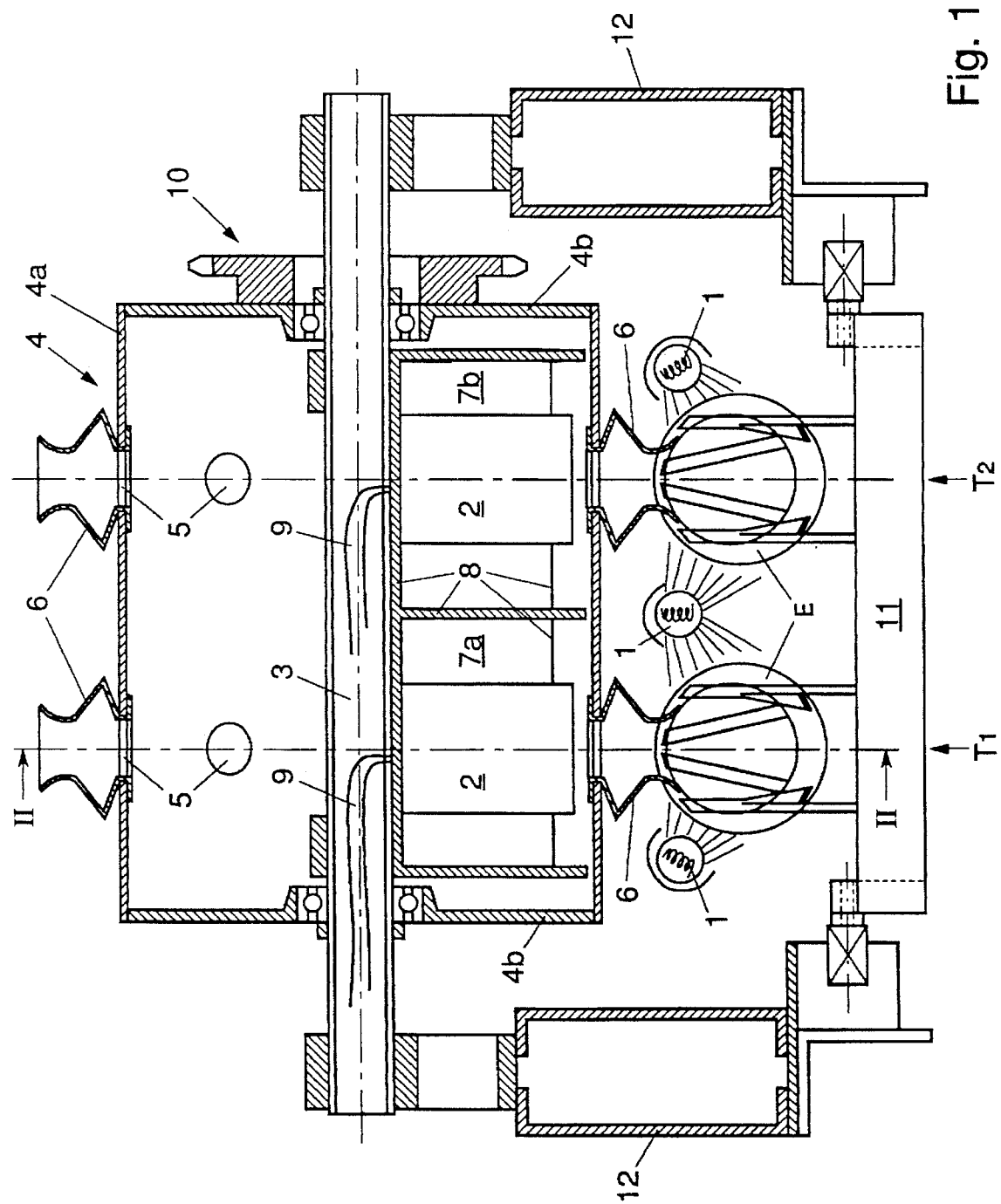
FIG. 1 shows an axial sectional view through the candler taken on the line I—I from FIG. 2.
Figure 2:
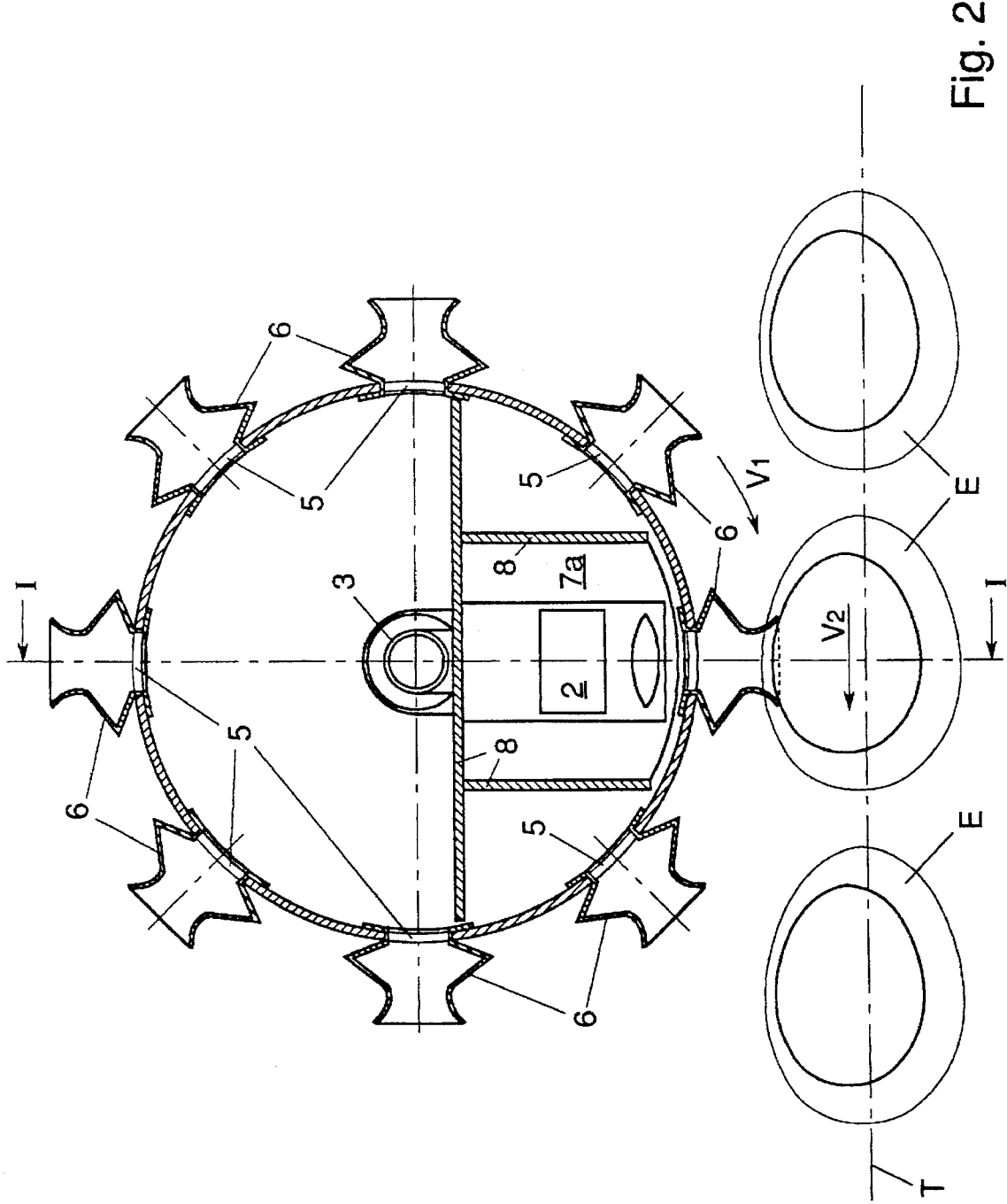
FIG. 2 shows a radial sectional view taken on the line II—II from FIG. 1.

The exemplary embodiment shown of the apparatus for candling eggs for the presence of blood, which eggs travel along a path T1, T2, comprises at least one light source 1 for shining on the egg E to be inspected, and detection means 2 for determining the amount of light falling through the egg. In order to prevent the detection means from receiving scattered light which has not passed the contents of an egg E to be inspected, according to the invention, the detection means 2 are accommodated in a lightproof drum 4 which is drivable for rotation around a fixed shaft 3. Provided in the surface 4a of the drum 4 are a number of light transmission openings 5, each having a bellows 6 manufactured from lightproof material. The bellows 6 is preferably slightly accordeon-shaped so as to enable it to set off differences in dimension between different eggs through a greater or lesser degree of compression. In operation, the drum 4 has a rotational speed so that the ends of the bellows 6 remote from the drum 4 have a speed v1 corresponding to the speed of travel v2 of the eggs to be inspected. The drum 4 with the bellows 6 are positioned relative to the path T1, T2 along which the eggs travel so that in operation, each time during a part of the path of travel T1, T2 of the eggs E, the bellows connect to an egg E to be inspected. Also, the detection means are positioned in the drum 4 so that they only receive light that falls into the drum 4 via the egg which is to be inspected and to which the bellows 6 connects, and via the light transmission opening 5 associated with that bellows.

In the present exemplary embodiment, the drum is provided with two series of light transmission openings, each located in a radial sectional plane P1, P2 of the drum 4, in which planes P1, P2 are also located the paths T1, T2 along which the eggs E travel. In the present exemplary embodiment, each series contains eight light transmission openings 5 with a corresponding number of bellows 6. In spite of the fact that the paths T1, T2 along which the eggs E travel are closely spaced, the two paths of eggs can still be candled simultaneously without scattered light coming from one candling measurement affecting the other candling measurement. Owing to the presence of the drum with the detectors 2 separately accommodated therein, the candler can be of a very compact design.

As is clearly shown in FIG. 1, the apparatus comprises a detector 2 for each series of light transmission openings 5.

Each detector 2 is contained in a compartment 7a, 7b of such design that it can only be entered by light coming from a light transmission opening 5 whose bellows 6 connects to an egg E to be inspected. The compartment 7a, 7b is bounded by the drum wall 4a, 4b and some lightproof partitions 8 connected to the fixed shaft 3. The presence of the partitions 8 prevents light from falling on the detection means 2 via other transmission openings 5, whose bellows do not connect to an egg to be inspected.

In a practical embodiment, the drum 4 is bearing-mounted on a hollow, fixed shaft 3, enabling the wiring 9, connecting the detection means to a processing or control device, to be included therein. The driving gear 10 of the drum 4 is synchronized with the driving gear of the conveyor 11 by means of which the eggs are moved along the or each path of travel T1, T2. In the exemplary embodiment shown, the driving gear 10 of the drum 4 is formed by a chain wheel which is dynamically coupled to a driving shaft of the conveyor 11.

The fixed shaft 3 is connected to a frame 12 which is coupled in a stable manner to the conveyor 11, as a result of which the relation between the drum 4 and the conveying paths T1, T2 is fixed.

The processing and/or control device to which the detection means 2 are connected is so designed that a measurement on an egg to be inspected is carried out at the moment when a bellows 6 connects in a completely lightproof manner to the egg E to be inspected. In this manner, a measurement can be carried out in some milliseconds without this measurement being affected by scattered light.

Consequently, the invention provides a highly compact apparatus for candling eggs, by means of which the eggs can be candled at great speed during continuous and discontinuous conveyance.

It is clear that the invention is not limited to the exemplary embodiment shown, but that various modifications are possible within the purview of the invention. For instance, the drum may be provided with more than two series of transmission openings 5 or with only one series of transmission openings 5. It goes without saying that the number of paths of travel is always equal to the number of series of transmission openings 5. The exemplary embodiment shown of the conveyor 11 comprises grippers for receiving the eggs, however it will be understood that the apparatus can also be used with a roller conveyor.

It is essential that through the presence of the drum, candling measurements can be carried out in a fast manner by means of a highly compact apparatus without the measurements being affected by scattered light.

I claim:

1. An apparatus for candling eggs travelling along a path for the presence of blood, comprising:

at least one light source for shining on an egg being inspected, detection means for determining the amount of light falling through the egg;

a lightproof drum rotatable around a fixed shaft, the detection means being housed in the drum, the drum having a number of light transmission openings in its surface, each of said openings having a bellows comprising a lightproof material, the drum in operation having a rotational speed such that ends of the bellows remote from the drum have a speed corresponding to speed of travel of the eggs being inspected, the bellows being positioned relative to a path along which the eggs travel such that in operation the bellows connect in a lightproof manner to an egg to be inspected during part of the eggs' travel, the detection means being positioned in the drum so as to only receive light that falls into the drum via the egg which is being inspected and to which the bellows connects, and via the light transmission opening associated with said bellows.

2. An apparatus according to claim 1, wherein the light transmission openings form part of at least one series of light transmission openings, the light transmission openings from one series being located in a radial sectional plane of the drum, the path along which the eggs travel being located in said radial sectional plane.

3. An apparatus according to claim 2, comprising a number of series of light transmission openings, the eggs travelling in paths parallel to the light transmission openings.

4. An apparatus according to claim 2, wherein the detection means comprises a detector for each series of light transmission openings, each of said detectors being located in a compartment which is only entered by light coming from a light transmission opening whose bellows connects to an egg being inspected.

5. An apparatus according to claim 4 wherein each compartment is bounded by a wall of the drum and lightproof partitions connected to the fixed shaft.

6. An apparatus according to claim 1 wherein the fixed shaft comprises a hollow shaft for housing wiring which connects the detection means to a processing or control device.

7. An apparatus according to claim 1 wherein a driving gear of the drum is synchronized with a driving gear of a conveyor which moves the eggs along the path of travel.

8. An apparatus according to claim 1, wherein a measurement on an egg being inspected is carried out at the moment when a bellows connects in a completely lightproof manner to the egg.

* * * * *